United States Patent [19]

Shankar

[11] Patent Number: 5,688,990
[45] Date of Patent: Nov. 18, 1997

[54] SUBSTITUTED AZETIDINONE COMPOUNDS USEFUL AS HYPOCHOLESTEROLEMIC AGENTS

[76] Inventor: Bandarpalle B. Shankar, 3405 Wellington Ct., Somerville, N.J. 08876

[21] Appl. No.: 444,167

[22] Filed: May 18, 1995

Related U.S. Application Data

[63] Continuation of Ser. No. 403,081, Mar. 13, 1995, Pat. No. 5,627,176, which is a continuation-in-part of Ser. No. 218, 498, Mar. 25, 1994, abandoned.

[51] Int. Cl.$^6$ ............................................... C07C 229/02
[52] U.S. Cl. ............................................................. 560/39
[58] Field of Search ................................ 562/435; 560/39

[56] References Cited

U.S. PATENT DOCUMENTS

| | | |
|---|---|---|
| 4,680,391 | 7/1987 | Firestone et al. . |
| 4,983,597 | 1/1991 | Yang et al. . |
| 5,120,729 | 6/1992 | Chabala et al. . |

FOREIGN PATENT DOCUMENTS

| | | |
|---|---|---|
| 199630 | 10/1986 | European Pat. Off. . |
| 264231 | 4/1988 | European Pat. Off. . |
| 337549 | 10/1989 | European Pat. Off. . |
| 93/02048 | 2/1993 | WIPO . |

OTHER PUBLICATIONS

Ram et al, *Indian J. Chem.*, Sect B, 29B, 12 (1990), pp. 1134–1137.
Witzum, *Circulation*, 80, 5 (1989), pp. 1101–1114.
Illingworth, *Drugs*, 36(Supp. 3) (1988), pp. 63–71.
Allain, et al, *Clin. Chem.*, 20, (1974), pp. 470–475.
Schnitzer–Polokoff, et al. *Comp. Biochem. Physiol.*, 99A (1991), pp. 665–670.
Horie, et al, *Atherosclerosis*, 88 (1991), pp. 183–192.
Baxter, et al, *J. Biological Chem.*, 267, 17 (1992), pp. 11705–11708.
*Current Drugs: Anti–Atherosclerotic Agents* –Summary Factfile, May, 1992.
Bose, et al, *J. Chem. Soc., Chem. Comm.*, 2 (1984), pp. 86–87.
Cossio, et al., *J. Chem. Soc., Chem. Comm.*, (1989), pp. 74–76.
Furukawa, et al, *Chem. Pharm. Bull.*, 26, 1 (1978), pp. 260–263.
*Chemical Abstracts*, 109, 5 (1988) abstract no. 38139j.
*Chemical Abstracts*, 114, 19 (1991) abstract No. 185021w.

*Primary Examiner*—Joseph Conrad
*Attorney, Agent, or Firm*—Anita W. Magatti

[57] ABSTRACT

Substituted azetidinone hypocholesterolemic agents of the formula

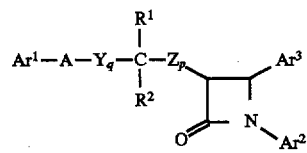

or a pharmaceutically acceptable salt thereof, wherein:

$Ar^1$ is $R^3$-substituted aryl;

$Ar^2$ is $R^4$-substituted aryl;

$Ar^3$ is $R^5$-substituted aryl;

Y and Z are independently —$CH_2$—, —CH(lower alkyl)- or —C(dilower alkyl)-;

A is —O—, —S—, —S(O)— or —$S(O)_2$—;

$R^1$ is —$OR^6$, —$O(CO)R^6$, —$O(CO)OR^9$ or —$O(CO)NR^6R^7$; $R^2$ is hydrogen, lower alkyl or aryl; or $R^1$ and $R_2$ together are =O;

q is 1, 2 or 3; p is 0, 1, 2, 3 or 4;

$R^5$ is 1–3 substituents independently selected from —$OR^6$, —$O(CO)R^6$, —$O(CO)OR^9$, —$O(CH_2)_{1-5}OR^9$, —$O(CO)NR^6R^7$, —$NR^6R^7$, —$NR^6(CO)R^7$, —$NR^6(CO)OR^9$, —$NR^6(CO)NR^7R^8$, —$NR^6SO_2$-lower alkyl, —$NR^6SO_2$-aryl, —$CONR^6R^7$, —$COR^6$, —$SO_2NR^6R^7$, $S(O)_{0-2}$-alkyl, $S(O)_{0-2}$-aryl, —$O(CH_2)_{1-10}$-$COOR^6$, —$O(CH_2)_{0-10}CONR^6R^7$, o-halogeno, m-halogeno, o-lower alkyl, m-lower alkyl, -(lower alkylene)-$COOR^6$ and —CH=CH—$COOR^6$;

$R^3$ and $R^4$ are 1–3 substituents independently selected from $R^5$, hydrogen, p-lower alkyl, aryl, —$NO_2$, $CF_3$ and p-halogeno;

$R^6$, $R^7$ and $R^8$ are hydrogen, lower alkyl, aryl or aryl-substituted lower alkyl; and $R^9$ is lower alkyl, aryl or aryl-substituted lower alkyl; are disclosed, as well as a method of lowering serum cholesterol by administering said compounds, pharmaceutical compositions containing them, the combination of a substituted azetidinone and a cholesterol biosynthesis inhibitor for the treatment and prevention of atherosclerosis, novel intermediates and methods for preparing said intermediates.

6 Claims, No Drawings

SUBSTITUTED AZETIDINONE COMPOUNDS USEFUL AS HYPOCHOLESTEROLEMIC AGENTS

This is a continuation of application Ser. No. 08/403,081, filed Mar. 13, 1995, now U.S. Pat. No. 5,627,176, which is a continuation-in-part of U.S. Ser. No. 08/218,498, filed Mar. 25, 1994, now abandoned.

BACKGROUND OF THE INVENTION

The present invention relates to substituted azetidinones useful as hypocholesterolemic agents in the treatment and prevention of atherosclerosis, to the combination of a substituted azetidinone of this invention and a cholesterol biosynthesis inhibitor for the treatment and prevention of atherosclerosis, to pharmaceutical compositions comprising said azetidinones and combinations, to a process for preparing intermediates useful in the synthesis of said azetidinones, and to the novel intermediates prepared by said process.

Atherosclerotic coronary heart disease represents the major cause for death and cardiovascular morbidity in the western world. Risk factors for atherosclerotic coronary heart disease include hypertension, diabetes mellitus, family history, male sex, cigarette smoke and serum cholesterol. A total cholesterol level in excess of 225–250 mg/dl is associated with significant elevation of risk.

Cholesteryl esters are a major component of atherosclerotic lesions and the major storage form of cholesterol in arterial wall cells. Formation of cholesteryl esters is also a key step in the intestinal absorption of dietary cholesterol.

A few azetidinone compounds have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in Indian J Chem., Sect. B. 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxoalkylidene)-2-azetidinones as blood platelet aggregation inhibitors. European Patent 199,630 and European Patent Application 337,549 disclose elastase inhibitory substituted azetidinones said to be useful in treating inflammatory conditions resulting in tissue destruction which are associated with various disease states, e.g. atherosclerosis. WO93/02048 discloses substituted β-lactams useful as hypocholesterolemic agents.

In addition to regulation of dietary cholesterol, the regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

The inhibition of cholesterol biosynthesis by 3-hydroxy-3-methylglutaryl coenzyme A reductase (EC1.1.1.34) inhibitors has been shown to be an effective way to reduce plasma cholesterol (Witzum, Circulation, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, Drugs, 36 (Suppl. 3) (1988), p. 63–71).

SUMMARY OF THE INVENTION

Compounds of the present invention are represented by the formula I

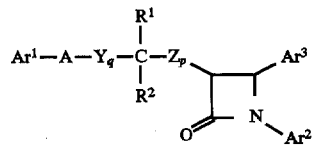

or a pharmaceutically acceptable salt thereof, wherein:

$Ar^1$ is $R^3$-substituted aryl;

$Ar^2$ is $R^4$-substituted aryl;

$Ar^3$ is $R^5$-substituted aryl;

Y and Z are independently selected from the group consisting of —$CH_2$—, —CH(lower alkyl)- and —C(dilower alkyl)-;

A is —O—, —S—, —S(O)— or —$S(O)_2$—;

$R^1$ is selected from the group consisting of —$OR^6$, —$O(CO)R^6$, —$O(CO)OR^9$ and —$O(CO)NR^6R^7$; $R^2$ is selected from the group consisting of hydrogen, lower alkyl and aryl; or $R^1$ and $R^2$ together are =O;

q is 1, 2 or 3;

p is 0, 1, 2, 3 or 4;

$R^5$ is 1–3 substituents independently selected from the group consisting of —$OR^6$, —$O(CO)R^6$, —$O(CO)OR^9$, —$O(CH_2)_{1-5}OR^9$, —$O(CO)NR^6R^7$, —$NR^6R^7$, —$NR^6(CO)R^7$, —$NR^6(CO)OR^9$, —$NR^6(CO)NR^7R^8$, —$NR^6SO_2$-lower alkyl, —$NR^6SO_2$-aryl, —$CONR^6R^7$, —$COR^6$, —$SO_2NR^6R^7$, $S(O)_{0-2}$-alkyl, $S(O)_{0-2}$-aryl, —$O(CH_2)_{1-10}$—$COOR^6$, —$O(CH_2)_{1-10}CONR^6R^7$, o-halogeno, m-halogeno, o-lower alkyl, m-lower alkyl, -(lower alkylene)-$COOR^6$, —CH=CH—$COOR^6$;

$R^3$ and $R^4$ are independently 1–3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferred are compounds of formula I wherein $Ar^1$ is $R^3$-substituted phenyl, especially (4-$R^3$)-substituted phenyl. $Ar^2$ is preferably $R^4$-substituted phenyl, especially (4-$R^4$)-substituted phenyl. $Ar^3$ is preferably $R^5$-substituted phenyl, especially (4-$R^5$)-substituted phenyl. Mono-substitution of each of $Ar^1$, $Ar^2$ and $Ar^3$ is preferred.

Y and Z are each preferably —$CH_2$—. $R^2$ is preferably hydrogen. $R^1$ is preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above). Also preferred are compounds wherein $R^1$ and $R^2$ together are =O.

The sum of q and p is preferably 1 or 2, more preferably 1. Preferred are compounds wherein p is zero and q is 1.

More preferred are compounds wherein p is zero, q is 1, Y is —CH$_2$— and R$^1$ is —OR$^6$, especially when R$^6$ is hydrogen.

Another group of preferred compounds is that wherein Ar$^1$ is R$^3$-substituted phenyl, Ar$^2$ is R$^4$-substituted phenyl and Ar$^3$ is R$^5$-substituted phenyl. Also preferred are compounds wherein Ar$^1$ is R$^3$-substituted phenyl, Ar$^2$ is R$^4$-substituted phenyl, Ar$^3$ is R$^5$-substituted phenyl, and the sum of p and q is 1 or 2, especially 1. More preferred are compounds wherein Ar$^1$ is R$^3$-substituted phenyl, Ar$^2$ is R$^4$-substituted phenyl, Ar$^3$ is R$^5$-substituted phenyl, p is zero and q is 1.

A is preferably —O—.

R$^3$ is preferably —COOR$^6$, —CONR$^6$R$^7$, —COR$^6$, —SO$_2$NR$^6$R$^7$, S(O)$_{0-2}$-alkyl, S(O)$_{0-2}$-aryl, NO$_2$ or halogeno. A more preferred definition for R$^3$ is halogeno, especially fluoro or chloro.

R$^4$ is preferably hydrogen, lower alkyl, —OR$^6$, —O(CO)R$^6$, —O(CO)OR$^9$, —O(CO)NR$^6$R$^7$, —NR$^6$R$^7$, COR$^6$ or halogeno, wherein R$^6$ and R$^7$ are preferably independently hydrogen or lower alkyl, and R$^9$ is preferably lower alkyl. A more preferred definition for R$^4$ is hydrogen or halogeno, especially fluoro or chloro.

R$^5$ is preferably —OR$^6$, —O(CO)R$^6$, —O(CO)OR$^9$, —O(CO)NR$^6$R$^7$, —NR$^6$R$^7$, -(lower alkylene)-COOR$^6$ or —CH=CH—COOR$^6$, wherein R$^6$ and R$^7$ are preferably independently hydrogen or lower alkyl, and R$^9$ is preferably lower alkyl. A more preferred definition for R$^5$ is —OR$^6$, -(lower alkylene)-COOR$^6$ or —CH=CH—COOR$^6$, wherein R$^6$ is preferably hydrogen or lower alkyl.

The invention also relates to a novel process for preparing chiral β-amino ester intermediates of formula II

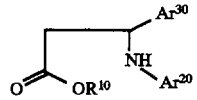
II wherein Ar$^{20}$ is Ar$^2$, a suitably protected hydroxy-substituted aryl or a suitably-protected amino-substituted aryl, Ar$^{30}$ is Ar$^3$, a suitably protected hydroxy-substituted aryl or a suitably-protected amino-substituted aryl, and —O(O)OR$^{10}$ is an acyl radical of a chiral alcohol, useful in the preparation of chiral 3-unsubstituted azetidinones of the formula

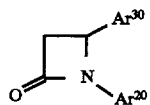
III wherein Ar$^{20}$ and Ar$^{30}$ are as defined above.

The process for preparing the compounds of formula II comprises:

reacting a bromoacetate of a chiral alcohol of the formula R$^{10}$OC(O)CH$_2$Br, wherein R$^{10}$OH is an optically pure chiral alcohol, an imine of the formula Ar$^{20}$—N=CH—Ar$^{30}$, wherein Ar$^{20}$ and Ar$^{30}$ are as defined above, and zinc to obtain a β-amino ester of formula II.

The intermediate of formula II can be converted to the chiral 3-unsubstituted azetidinone of formula III by cyclizing the β-amino ester of formula II with a Grignard reagent.

This invention also relates to novel intermediates of formula II, that is, compounds of formula II

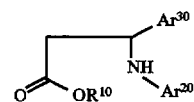
II wherein Ar$^{20}$ is R$^4$-substituted aryl, a suitably protected hydroxy-substituted aryl or a suitably-protected amino-substituted aryl;

Ar$^{30}$ is R$^5$-substituted aryl, a suitably protected hydroxy-substituted aryl or a suitably-protected amino-substituted aryl;

—C(O)OR$^{10}$ is an acyl radical of an optically pure chiral alcohol selected from the group consisting of 1-menthyl, isopino-campheyl, (1S)-endo-bornyl, isomenthyl, trans-2-phenylcyclo-hexyl or phenylmenthyl;

R$^5$ is 1–3 substituents independently selected from the group consisting of —OR$^6$, —O(CO)R$^6$, —O(CO)OR$^9$, —O(CH$_2$)$_{1-5}$OR$^9$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$-lower alkyl, —NR$^6$SO$_2$-aryl, —CONR$^6$R$^7$, —COR$^6$, —SO$_2$NR$^6$R$^7$, S(O)$_{0-2}$-alkyl, S(O)$_{0-2}$-aryl, —O(CH$_2$)$_{1-10}$-COOR$^6$, —O(CH$_2$)$_{1-10}$CONR$^6$R$^7$, o-halogeno, m-halogeno, o-lower alkyl, m-lower alkyl, -(lower alkylene)-COOR$^6$, —CH=CH—COOR$^6$;

R$^4$ is 1–3 substituents independently selected from the group consisting of R$^5$, H, p-lower alkyl, aryl, —NO$_2$, —CF$_3$ and p-halogeno;

R$^6$, R$^7$ and R$^8$ are independently selected from the group consisting of H, lower alkyl, aryl and aryl-substituted lower alkyl; and R$^9$ is lower alkyl, aryl or aryl-substituted lower alkyl.

This invention also relates to the use of a compound of formula I as a hypocholesterolemic agent for reducing plasma cholesterol levels and treating or preventing atherosclerosis in a mammal in need of such treatment.

In another aspect, the invention relates to a pharmaceutical composition comprising a substituted azetidinone of formula I in a pharmaceutically acceptable carrier. The invention also relates to the use of said pharmaceutical composition as a hypocholesterolemic agent for reducing plasma cholesterol levels and treating or preventing atherosclerosis, and to a method of preparing said compositions by admixing a compound of formula I and a pharmaceutically acceptable carrier.

The present invention also relates to a method of reducing plasma cholesterol levels, and to a method of treating or preventing atherosclerosis, comprising administering to a mammal in need of such treatment an effective amount of a combination of a substituted azetidinone cholesterol absorption inhibitor of this invention and a cholesterol biosynthesis inhibitor. That is, the present invention relates to the use of a substituted azetidinone cholesterol absorption inhibitor for combined use with a cholesterol biosynthesis inhibitor (and, similarly, use of a cholesterol biosynthesis inhibitor for combined use with a substituted azetidinone cholesterol absorption inhibitor) to treat or prevent athersclerosis or to reduce plasma cholesterol levels.

In yet another aspect, the invention relates to a pharmaceutical composition comprising an effective amount of a substituted azetidinone cholesterol absorption inhibitor, a cholesterol biosynthesis inhibitor, and a pharmaceutically acceptable carrier. The use of said composition to treat or prevent athersclerosis or to reduce plasma cholesterol levels is also contemplated, as is the preparation of said composition by admixing a substituted azetidinone cholesterol absorption inhibitor, a cholesterol biosynthesis inhibitor, and a pharmaceutically acceptable carrier. In a final aspect, the invention relates to a kit comprising in one container an effective amount of a substituted azetidinone cholesterol absorption inhibitor in a pharmaceutically acceptable carrier, and in a separate container, an effective amount of a cholesterol biosynthesis inhibitor in a pharmaceutically acceptable carrier.

DETAILED DESCRIPTION

As used herein, the term "lower alkyl" means straight or branched alkyl chains of 1 to 6 carbon atoms. Similarly, "lower alkylene" means a divalent alkyl chain, straight or branched, of 1 to 6 carbon atoms.

"Aryl" means phenyl, naphthyl, indenyl, tetrahydronaphthyl or indanyl.

"Halogeno" refers to fluoro, chloro, bromo or iodo radicals.

The above statement, wherein $R^6$, $R^7$ and $R^8$ are said to be independently selected from a group of substituents, means that $R^6$, $R^7$ and $R^8$ are independently selected, but also that where an $R^6$, $R^7$ or $R^8$ variable occurs more than once in a molecule, those occurrences are independently selected (e.g., if $R^1$ is —$OR^6$ wherein $R^6$ is hydrogen, $R^4$ can be —$OR^6$ wherein $R^6$ is lower alkyl). Similarly, $R^3$, $R^4$ and $R^5$ are independently selected from a group of substituents, and where more than one $R^3$, $R^4$ and/or $R^5$ is present, the substitutents are independently selected; those skilled in the art will recognize that the size and nature of the substituent (s) will affect the number of substituents which can be present.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin and CI-981; HMG CoA synthetase inhibitors, for example L-659,699 ((E,E-11-[3′R-(hydroxy-methyl)-4′-oxo-2′R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3′-bithiophen-5-yl)methoxy]benzene-methanamine hydrochloride). Preferred HMG CoA reductase inhibitors are lovastatin, pravastatin and simvastatin.

Compounds of formula I can be prepared by known methods. For example, the preparation of compounds of formula I, wherein $Ar^1$, $Ar^2$, $Ar^3$, $R^2$ and $Z_p$ are as described above, Y is —$CH_2$—, q is 1, $R^1$ is OH, and A is —O— or —S— (i.e., a compound of formula Ia), is described in Method 1:

Method 1

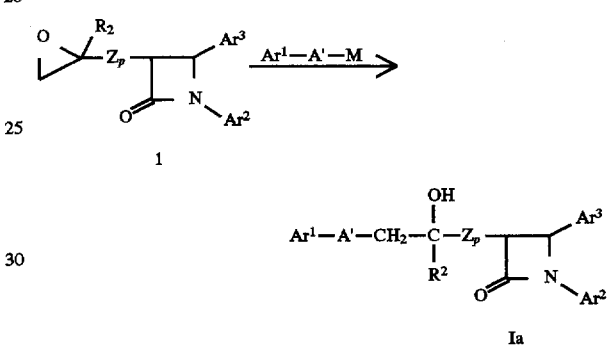

An epoxide-substituted azetidinone of formula 1 can be treated with a compound of formula $Ar^1$—A'—M, wherein A' is —O— or —S—, and wherein M is a metal such as sodium, potassium, lithium or magnesium, in an inert solvent such as tetrahydrofuran (THF) at room temperature and under an inert atmosphere such as $N_2$ to obtain a compound of formula Ia. Compounds of formula 1 are prepared immediately before the reaction by treating a solution of $Ar^1$—OH or $Ar^1$—SH in an inert solvent such as THF with a suspension of alkali metal hydride, or, when M is magnesium, a solution of an alkyl Grignard reagent such as isopropylmagnesium bromide, in the same solvent.

Alternatively, a compound of formula 1 can be treated with $Ar^1$—OH or $Ar^1$—SH in the presence of a reagent such as $ZnCl_2$ to obtain a compound of formula Ia.

Preparation of the starting materials of formula 1 is shown by the following processes (exemplifying compounds wherein p is 0, i.e., Z is not present), wherein Process A prepares compounds of formula 1a, having relative "trans" orientation at the β-lactam 3- and 4-positions, and wherein Process B prepares compounds of formula 1b, having relative "cis" orientation at the β-lactam 3- and 4-positions:

Process A:

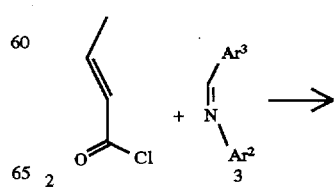

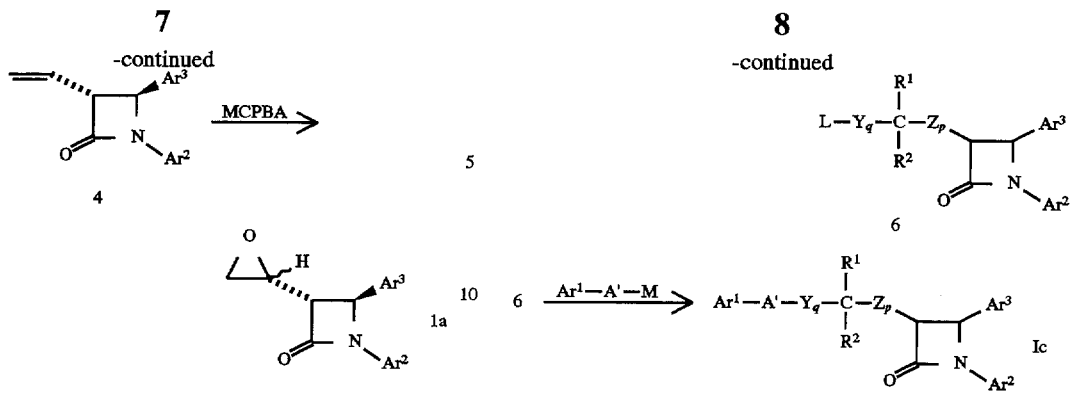

In the first step, crotonyl chloride (2) is refluxed with an imine of formula 3, wherein $Ar^2$ and $Ar^3$ are as defined above, in an inert solvent such as $CH_2Cl_2$ or THF in the presence of a base such as tri-n-butyl amine, triethylamine or diisopropylethylamine to obtain a trans-substituted 3-vinyl-2-azetidinone of formula 4. The compound of formula 4 is then treated with an oxidizing agent such as MCPBA in an inert solvent such as $CH_2Cl_2$, the reaction is quenched with a reagent such as aqueous $Na_2SO_3$ and conventional extraction and separation techniques are used to obtain a mixture of 3-oxiranyl-2-azetidinone epimers which can be separated by HPLC.

Process B:

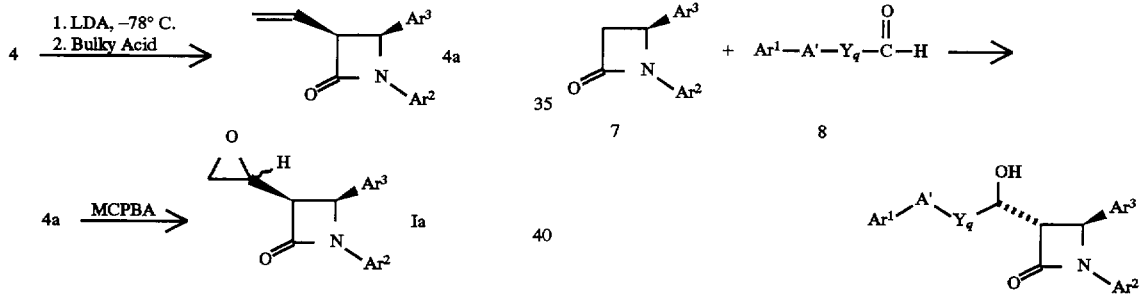

The 3-vinyl-2-azetidinone of formula 4 can be treated with a strong base such as lithium diisopropylamide (LDA) in a suitable solvent such as THF at low temperatures, e.g., −78° C., followed by treatment with a bulky acid such as 2,6-di-tert-butyl-4-methylphenol (BHT), glacial acetic acid or isovaleric acid, to obtain the corresponding cis-3-vinyl-2-azetidinone (4a). The compound of formula 4a can be oxidized in a manner similar to that described in Process A to obtain the compound of formula Ib.

The following Method 2 describes the preparation of compounds of formula I wherein $Ar^1$, $Ar^2$, $Ar^3$, $R^1$, $R^2$, $Y_q$ and $Z_p$ are as described above, and A is —O— or —S— (i.e., a compound of formula Ic):

Method 2:

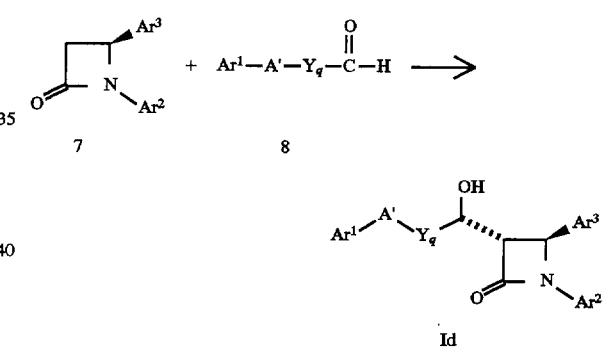

An activated carboxylic acid derivative of formula 5, for example an acid chloride, wherein Q is chloro, and wherein L is a leaving group such as a halide, can be reacted with an imine of formula 3 in the presence of a base such as a trialkylamine (e.g., triethylamine or tri-n-butylamine) at room temperature or elevated temperature in an inert solvent such as $CH_2Cl_2$ or toluene. The intermediate of formula 6 is then reacted with a compound of formula $Ar^1$—A'—M as described in Method 1 to obtain a compound of formula Ic.

Method 3 describes the preparation of compounds of formula Id wherein $Ar^1$, $Ar^2$, $Ar^3$ and $Y_q$ are as described above, $R^1$ is OH, $R^2$ is H, p is zero and A' is —O— or —S—:

Method 3:

A 3-unsubstituted azetidinone of formula 7 is treated with a strong base such as LDA or lithiumdicyclohexylamide at low temperatures (e.g. −70° to −78° C.) in an inert solvent such as THF, followed by reaction with an aldehyde of formula 8. When the 3-unsubstituted azetidinone is chiral, the products of the reaction with aldehyde 8 are non-racemic.

Starting materials of formulae 2, 3, 5, 7 and 8 are known or are prepared by methods known in the art.

Chiral starting materials of formula III, of which 7 is an example, can be prepared by cyclizing chiral β-amino ester intermediates of formula II, which intermediates are prepared by the novel process described above. The procedure for preparing compounds of formula III is shown in the following reaction scheme:

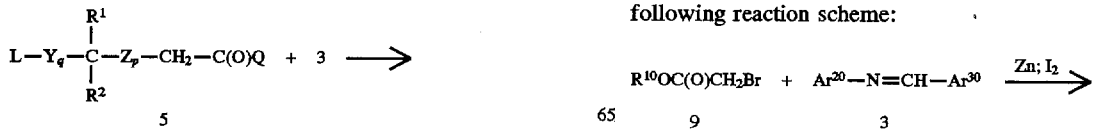

-continued

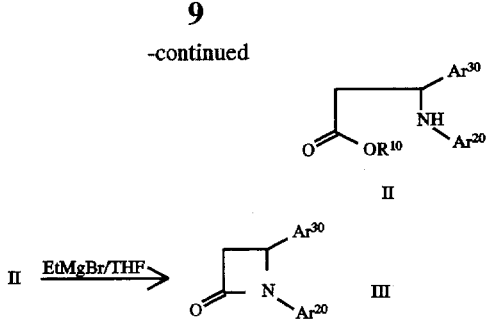

wherein Ar$^{20}$, Ar$^{30}$ and R$^{10}$ are as defined above. Suitable protecting groups for the hydroxy- or amino-substituted aryl groups in Ar$^{20}$ and Ar$^{30}$ are exemplified in the table below. Typical R$^{10}$OH optically pure chiral alcohols are selected from the group consisting of 1-menthyl, isopino-campheyl, (1S)-endo-bornyl, isomenthyl, trans-2-phenylcyclo-hexyl and phenylmenthyl. For preparing the preferred compounds of formula III, the preferred optically pure alcohols are 1-menthyl, (−)isopino-campheyl, (1S)-endo-(−)bornyl, (+)isomenthyl, (−)-trans-2-phenylcyclo-hexyl and (−)phenylmenthyl.

In the first step, equimolar amounts of a bromoacetate of formula 9 and an imine of formula 3 are reacted with zinc dust in an inert solvent such as anhydrous dioxane, THF or diethyl ether, preferably in the presence of a zinc activating agent such as iodine, at a temperature of 10° to 30°, preferably 23° to 25° C. for about 24 to 48 hours. The reaction is also preferably carried out with ultrasonification. The resultant β-amino ester is purified by conventional methods, for example the zinc dust is filtered off, the excess imine is crystallized out, and the β-amino ester is then crystallized out; additional β-amino ester can be recovered by flash chromatography.

In the second step, the β-amino ester is cyclized by treatment with a Grignard reagent such as isopropylmagnesium bromide or ethylmagnesium bromide in an ethereal solvent such as THF at −40° to 40° C., preferably at 0° C. to room temperature.

After cyclization, protecting groups can be removed as necessary by procedures well known to those skilled in the art.

Starting materials of formula 9 are prepared by reacting the sodium alkoxide of the corresponding chiral alcohol with bromo acetyl chloride at −40° C. to room temperature, preferably −20° C. to room temperature in an inert solvent such as THF or diethyl ether.

For various chiral alcohol starting materials, the following enantiomeric ratios were observed in the corresponding 3-unsubstituted azetidinones:

| Chiral alcohol | Ratio |
|---|---|
| Menthol | 60:40 |
| Borneol | 60:40 |
| Isomenthol | 75:25 |
| Isopinocampheol | 75:25 |
| Phenyl cyclohexanol | 99:1 |
| Phenyl menthol | 99:1 |

Compounds of formula I wherein A is —S(O)— or —S(O)$_2$— can be prepared by treating the corresponding compound wherein A is —S— with an oxidizing agent such as m-chloroperoxybenzoic acid (MCPBA).

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \>NH | \>NCOalkyl, \>NCObenzyl, \>NCOphenyl |
| | \>NCH$_2$OCH$_2$CH$_2$Si(CH$_3$)$_3$, \>NC(O)OC(CH$_3$)$_3$, |
| | \>N-benzyl, \>NSi(CH$_3$)$_3$, \>NSi—C(CH$_3$)$_3$ with CH$_3$/CH$_3$ |
| —NH$_2$ | —N(succinimidyl) |
| —OH | —OCH$_3$, —OCH$_2$OCH$_3$, —OSi(CH$_3$)$_3$, —OSi—C(CH$_3$)$_3$ with CH$_3$/CH$_3$ or —OCH$_2$phenyl |

We have found that the compounds of this invention lower serum lipid levels, in particular serum cholesterol levels. Compounds of this invention have been found to inhibit the intestinal absorbtion of cholesterol and to significantly reduce the formation of liver cholesteryl esters in animal models. Thus, compounds of this invention are hypocholesterolemic agents by virtue of their ability to inhibit the esterification and/or intestinal absorption of cholesterol; they are therefore useful in the treatment and prevention of atherosclerosis in mammals, in particular in humans.

In addition to the compound aspect, the present invention therefore also relates to a method of lowering serum cholesterol levels, which method comprises administering to a mammal in need of such treatment a hypocholesterolemic effective amount of a compound of formula I of this invention. The compound is preferably administered in a pharmaceutically acceptable carrier suitable for oral administration.

The present invention also relates to a pharmaceutical composition comprising a compound of formula I of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 to about 2000 mg of drug per day, preferably about 5 to about 1000 mg, given in a single dose or 2–4 divided doses. The exact dose, however, is determined by the attending clinician and is dependent on the potency of the compound administered, the age, weight, condition and response of the patient.

For the combinations of this invention wherein the substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2 g per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a substituted azetidinone absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing 3-unsubstituted azetidinones starting materials and compounds of formula I. The stereochemistry listed is relative stereochemistry unless otherwise noted. The terms cis and trans refer to the relative orientations at the β-lactam 3- and 4-positions.

Preparation 1

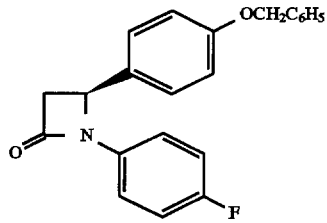

Step 1:
Preparation of (+)-trans-2-phenyl cyclohexylbromoacetate Dissolve (+)-trans-2-phenyl cyclohexanol (0.0113 mole) in anhydrous THF, cool to −15° C., add NaH (1.2 eq.) in portions and stir for 30 min. Add bromoacetyl chloride (1.5 eq.) dropwise and stir overnight at room temperature. Cool the reaction mixture to 0° C. and quench with t-butanol (5 mL) and water, dropwise (10 mL). Warm the mixture to room temperature, dilute with ethyl acetate (EtOAc) and wash in sequence with water (2×50 mL) and brine (2×50 mL). Dry the organic layer over MgSO$_4$, filter and concentrate. Purify the resultant residue by flash silica gel chromatography, eluting with hexane→5% EtOAc/hexane.

Step 2:
Preparation of

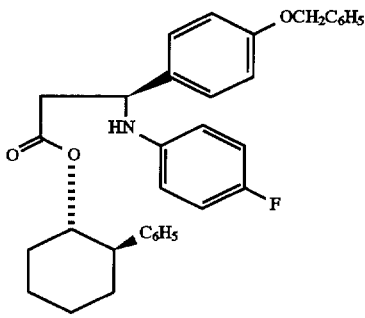

Reflux a solution of Zn dust (2.88 g, 44 mmol) and iodine (0.3 g, 1.2 mmol) in anhydrous dioxane (50 mL) for 1 h, then cool to room temperature. Immerse the flask in an ultrasonification bath, add a mixture of the product of step 1 (7.4 mmol) and 4-benzyloxybenzylidine-(4-fluoro)aniline (1.87 g, 6 mmol) and sonicate for 48 h at room temperature. Filter off the zinc dust over celite and concentrate the filtrate. Redissolve the resultant residue in a minimum amount of EtOAc; after 1 h, filter out the crystallized unreacted imine. Concentrate the filtrate under vacuum and redissolve the resulting residue in a minimum amount of CH$_3$OH to crystallize out the desired β-amino ester (1.2 g, 2.2 mmol). Concentrate the mother liquor and flash chromatograph it on silica gel, eluting with 10% hexane/EtOAc to obtain additional β-amino ester (0.3 g). M.p. 129°–131° C.; elemental analysis calc'd for C$_{34}$H$_{34}$FNO$_3$ is C, 78.01; H, 6.50; N, 2.67; found C, 77.62; H, 6.65; N, 2.74.

Step 3:
Treat a solution of the product of step 2 (0.18 mmole) in THF (5 mL) at 0° C. with ethylmagnesium bromide (1.2 eq.), stir for 4 h and allow the reaction to warm to room temperature. Quench the reaction with aqueous NH$_4$Cl (10 mL) and extract with ether (50 mL). Dry the organic layer over MgSO$_4$ and concentrate. Isolate the product by preparative chromatography on a silica gel plate, eluting with 20% EtOAc/hexane. Analyze the product using a chiral analytical HPLC AS column, eluting with i-propanol:hexane (20/80): the retention times for the two enantiomers were 15.3 and 16.4 min at a flow rate of 0.5 mL/min.

EXAMPLE 1

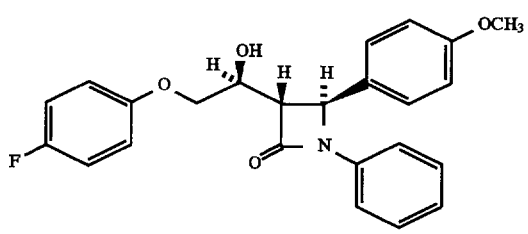

Step 1:

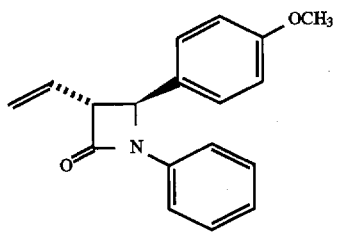

Add a solution of crotonyl chloride (1.81 mL, 0.02 moles) in CH$_2$Cl$_2$ (50 mL) dropwise, over a period of 1 h, to a refluxing solution of tri-n-butyl amine (7.23 mL, 0.03 moles) and p-methoxybenzylidine aniline (3.19 g, 0.015 moles) in CH$_2$Cl$_2$ (100 mL). Reflux for 16 h after the addition is complete, then cool to room temperature. Wash with water (2×100 mL) and saline (1×100 mL), then dry over Na$_2$SO$_4$, filter and concentrate. Stir the resultant oil with excess hexane and filter to obtain a yellow solid (2.5 g). Purify the residue by silica gel chromatography, eluting with EtOAc/hexane (1:5) to obtain a white solid (2.0 g, 49% yield), m.p. 119°–120° C., ELMS: M$^+$=279.

Step 2:

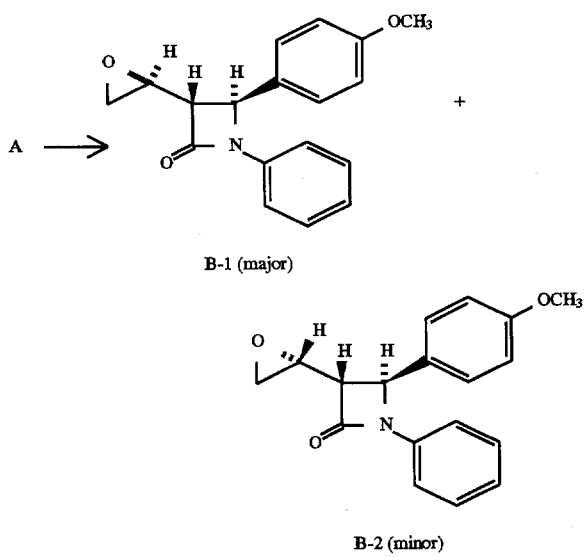

To a stirred solution of the product of Step 1 (compound A) (1.0 g, 0.0036 moles) in CH$_2$Cl$_2$ (40 mL) at room temperature, add MCPBA (1.9 g, 0.01 moles) portionwise. After 36 h, quench the reaction by dropwise addition of aqueous 10% Na$_2$SO$_3$. Separate the aqueous layer and wash the organic layer consecutively with 5% NaHCO$_3$ (2×50 mL), water (1×50 mL) and saline (1×50 mL), dry over Na$_2$SO$_4$ and concentrate. Purify the resultant residue by silica gel chromatography, eluting with EtOAc/hexane (2:1), to obtain a mixture of epoxide epimers as an off-white solid (1.00 g, 96% yield). Purify further by HPLC, eluting with 5% EtOAc/CH$_2$Cl$_2$ to obtain:

less polar epoxide: 0.27 g, m.p. 85°–88° C., EIMS: M$^+$295.

more polar epoxide: 0.54 g, m.p. 138°–141° C., EIMS: M$^+$295.

Step 3:

To a suspension of NaH (0.53 g of 60% dispersion in oil, 0.013 moles) in THF (35 mL) at room temperature, add 4-fluorophenol (2.26 g, 0.02 moles) and stir 30 min. until a clear solution is obtained. Add the major product of Step 2 (compound B-1) (2.0 g, 0.0067 moles) and stir at room temperature for 3 days. Dilute the reaction mixture with EtOAc, wash with water (1×30 mL), then saline (2×3 mL), dry over Na$_2$SO$_4$, filter and concentrate to obtain a brown oil (3.1 g). Purify the oil by silica gel chromatography, eluting with EtOAc/hexane (1:2) to obtain the title compound as a racemic mixture (1.23 g, 45% yield) (Rel (1'S,3S,4S)-1-phenyl-3-[1 hydroxy-2-(4-fluorophenoxy)ethyl]-4-(4-methoxyphenyl)-2-azetidinone).

Resolve the racemate from Step 3 using a preparative Chiracel® AS HPLC column, eluting with hexane-isopropanol (80:20) to give:

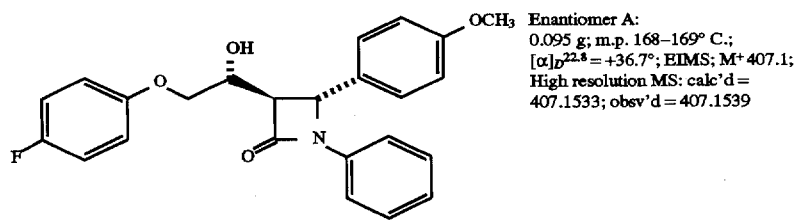

Enantiomer A:
0.095 g; m.p. 168–169° C.;
[α]$_D^{22.8}$ = +36.7°; EIMS; M$^+$ 407.1;
High resolution MS: calc'd = 407.1533; obsv'd = 407.1539

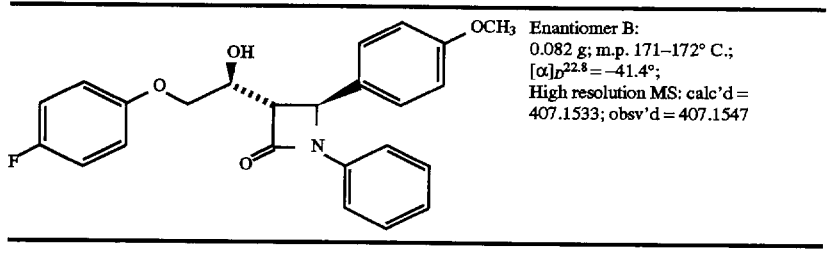

Enantiomer B:
0.082 g; m.p. 171–172° C.;
[α]$_D^{22.8}$ = –41.4°;
High resolution MS: calc'd = 407.1533; obsv'd = 407.1547

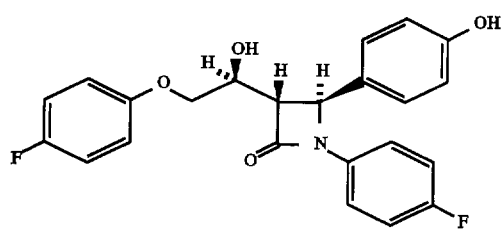

Step 1:

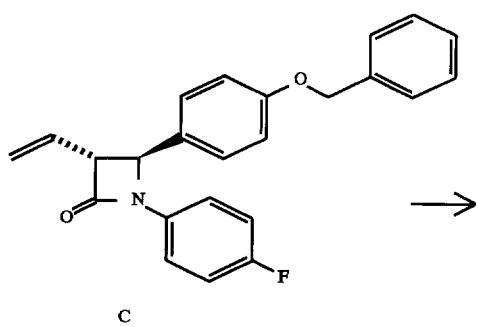

C

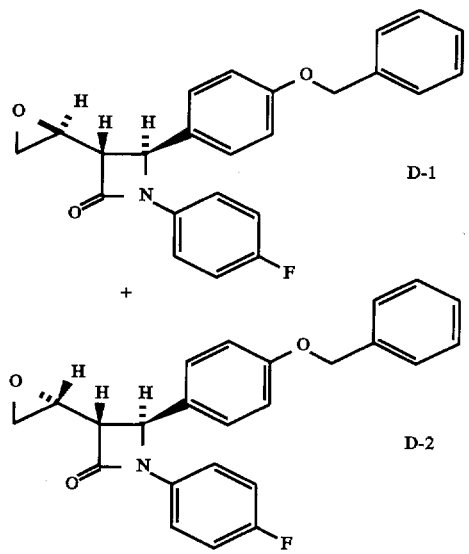

D-1

+

D-2

To a solution of compound C (5.0 g, 13.4 mmols) in CH$_2$Cl$_2$ (70 mL), add MCPBA (7 g, 40 mmols) and NaHCO$_3$ (3 g). Stir under N$_2$ for 36 hr (reaction about 95% complete), then add a small amount of (CH$_3$)$_2$S (approx. 1 mL) and stir for 30 min. Extract acidic by-products into aqueous NaHCO$_3$ solution and discard. Wash the organic layer with brine, dry over MgSO$_4$ and remove the solvent under vacuum. Purify the crude residue by silica gel chromatography, eluting with 20% ethyl acetate (EtOAc)/hexane→30% EtOAc/hexane to obtain:

isomer 1 (compound D-1), 1.7 g, EIMS: M$^+$=389;

isomer 2 (compound D-2), 2.3 g, EIMS: M$^+$=389.

Step 2:

D-1 →

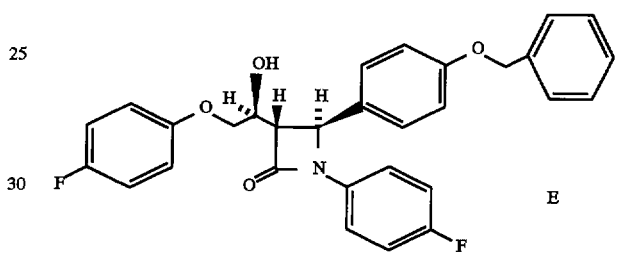

E

To a solution of 4-fluorophenol (0.715 g, 6.38 mmols) in THF (20 mL), add a suspension of 80% NaH (100 mg, 3.5 mmols, prewashed with hexane) in THF. After the bubbling ceases, to this solution, add a solution of the product of Step 1 (compound D-1) (0.45 g, 0.00115 moles) in THF and keep the reaction under N$_2$ at room temperature for 2 days. Treat the reaction mixture with aqueous Na$_2$CO$_3$ (20 mL), extract the product with EtOAc, dry over MgSO$_4$ and remove the solvent under vacuum. Purify the resultant residue by silica gel chromatography, eluting with 5% EtOAc/CH$_2$Cl$_2$→40% EtOAc/CH$_2$Cl$_2$.

Step 3:

Treat a solution of the product of Step 2 (compound E) (0.185 g, 0.00037 moles) in ethanol with 10% Pd/C (120 mg). Stir under aspirator vacuum, then introduce N$_2$ gas, repeating this procedure several times to eliminate oxygen. Introduce hydrogen gas and maintain at 1 atm for 18 h. Remove hydrogen under vacuum and reintroduce N$_2$. Filter the reaction mixture through Celite® and concentrate to a glass. Purify by preparative TLC, eluting with 15% EtOAc/CH$_2$Cl$_2$ to obtain 0.102 g of the title compound (rel (1'S,3S,4S)-1-(4-fluorophenyl)-3-[1-hydroxy-2-[4-fluorophenoxy]ethyl]-4-(4-hydroxyphenyl)-2-azetidinone). HRMS FAB: C$_{23}$H$_{20}$NO$_4$F$_2$ (M$^+$1) calc 412.1360; found 412.1368. Elemental analysis: Calculated: C=67.15, H=4.64, N=3.41, F=9.25; Found: C=67.00, H=4.87, N=3.26, F=9.09.

Racemic 1-(4-fluorophenyl)-3-[1-hydroxy-2-[4-fluorophenoxy]ethyl]-4-(4-hydroxyphenyl)-2-azetidinone is resolved using a preparative Chiracel® AS HPLC column, eluting with hexane-isopropanol (70:30) to give:

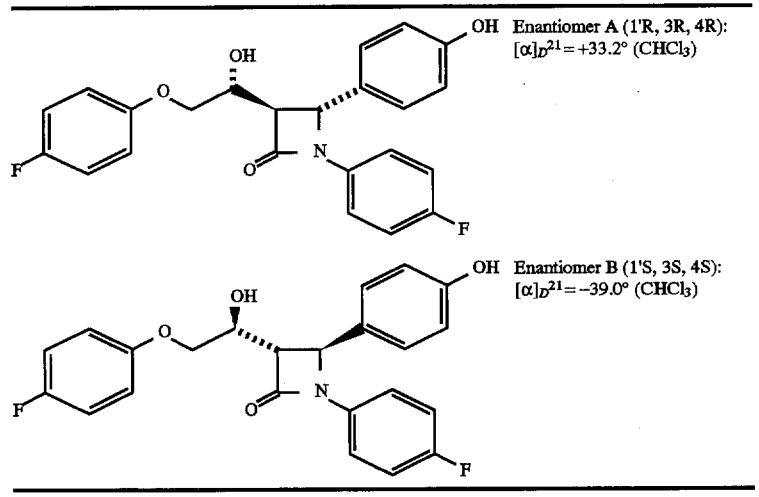

EXAMPLE 5

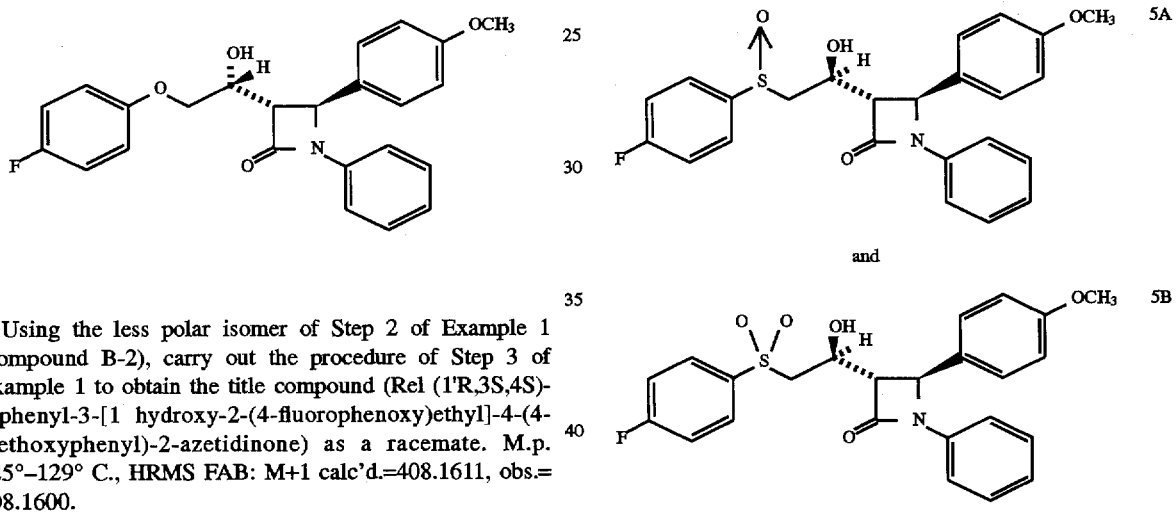

Using the less polar isomer of Step 2 of Example 1 (compound B-2), carry out the procedure of Step 3 of Example 1 to obtain the title compound (Rel (1'R,3S,4S)-1-phenyl-3-[1 hydroxy-2-(4-fluorophenoxy)ethyl]-4-(4-methoxyphenyl)-2-azetidinone) as a racemate. M.p. 125°–129° C., HRMS FAB: M+1 calc'd.=408.1611, obs.= 408.1600.

EXAMPLE 4

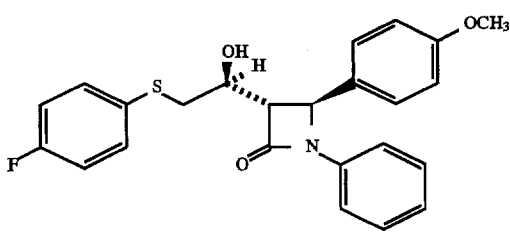

Use a procedure similar to Example 1, Step 3, substituting 4-fluorothiophenol for 4-fluorophenol and diluting with ether instead of EtOAc. After concenrating the extracted product, crystallize from ether-hexane to obtain a white solid (0.3 g, 70%), m.p. 129°–130° C., MS: HRMS FAB: calc'd. 424.1383, found 424.1394.

To a solution of the product of Example 4 (0.27 g, 0.637 mmols) in $CH_2Cl_2$ (20 mL) at 0° C., add MCBPA (0.12 g, 0.695 mmols) in portions and stir for 2 h. Quench the reaction with $(CH_3)_2S$ (0.5 mL), dilute with $CH_2Cl_2$, wash with 5% $NaHCO_3$ (2×20 mL), water (1×20 mL) and saline (1×20 mL), dry over $Na_2SO_4$, filter and concentrate. Purify the resultant residue by silica gel chromatography, eluting with EtOAc/hexane (1:1) and (2:1) to obtain two components:

5A, more polar component: 0.22 g;

5B, less polar component: 0.0259 g, HRMS FAB: calc'd. 456.1281, obs. 456.1280.

Further purify 5A by HPLC, eluting with 25% hexane/EtOAc to obtain isomers A and B:

Isomer A (less polar, 5A-1): m.p. 141°–143° C.; HRMS FAB: calc'd. 440.1332, obs. 440.1348;

Isomer B (more polar, 5A-2): m.p. 176°–179° C.; HRMS FAB: calc'd. 440.1332, obs. 440.1352.

EXAMPLE 6

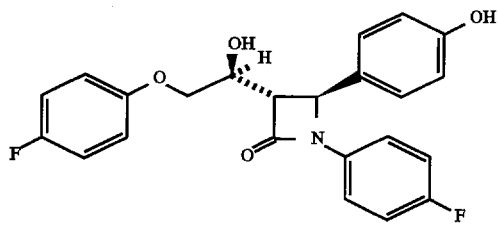

Step 1:

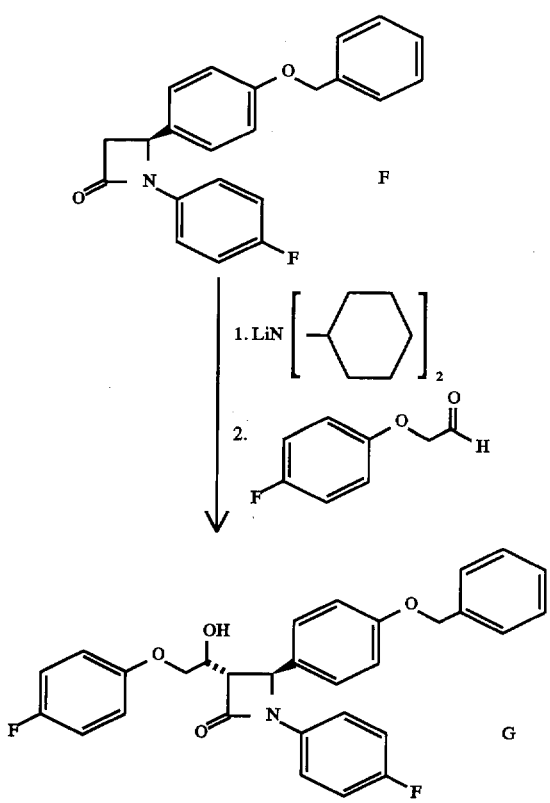

Prepare a solution of lithiumdicyclohexylamide (5.7 mmols) in THF (40 mL) by treating a cold (0° C.) solution of dicyclohexylamine in THF with 1 eq. of n-butyllithium (5.7 mmols, 3.6 mL of 1.6M hexane solution). Cool the solution to −70° C. and add a pre-cooled (−70° C.) solution of compound F (1.74 g, 5 mmols) in THF via cannula. After 15 min., slowly, and with stirring, add a solution of 4-fluorophenoxyacetaldehyde (1 g, 6.5 mmols) in THF. After 30 min. at −78° C., quench the reaction with glacial acetic acid (0.6 mL). Extract the product into ether, wash the ether layer with aqueous NaHCO$_3$, dry over MgSO$_4$ and evaporate the solvent under vacuum. Purify the resultant residue by chromatography on silica gel, eluting with 3:1 hexane/EtOAc→1:1 EtOAc/hexane. Concentrate the desired fractions to obtain three compounds, G1, G2 and G3:

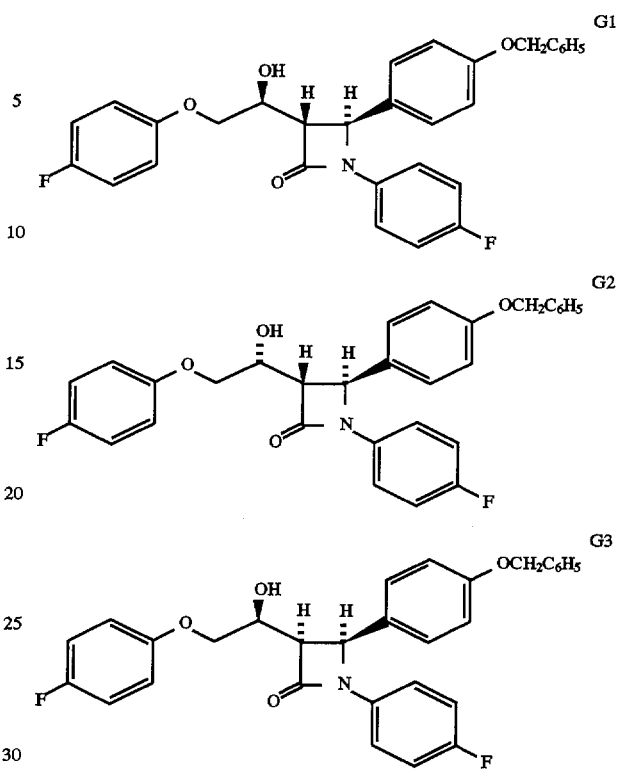

Step 2:

Use a procedure similar to that described in Example 2, Step 3 to remove the benzyl group from compounds G1, G2 and G3 to obtain compounds 6a, 6b and 6c:

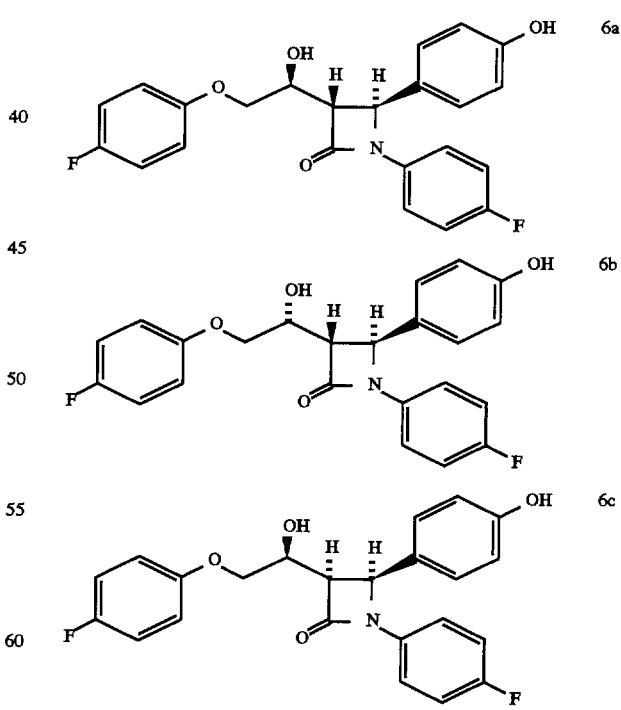

Separate racemic compound 6a into its enantiomers by chromatography on a Chiracel® AS preparative HPLC column, eluting with hexane/isopropyl alcohol (70:30). (Compound 6a is the same as the product of Example 2).

6b: M.p. 130°–131° C.
6c: HRMS FAB: calc'd. 412.1360, obs. 412.1364.

EXAMPLE 7

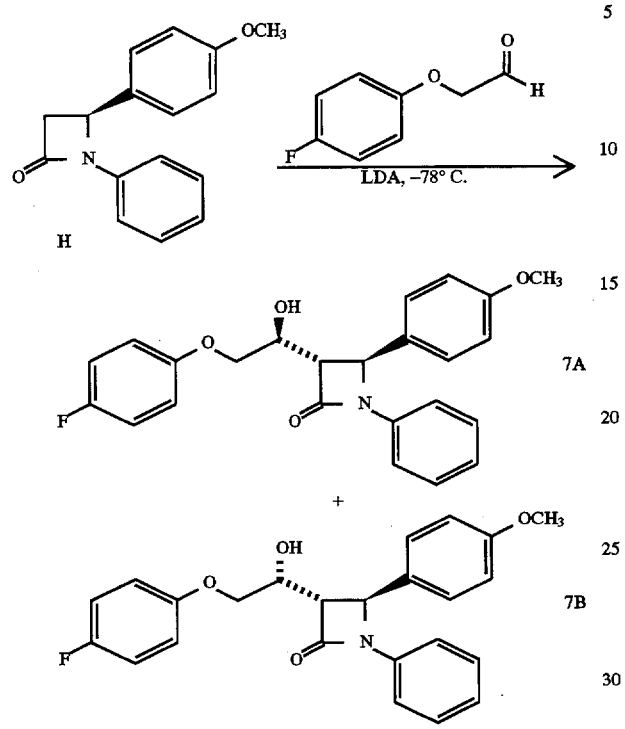

The azetidinone, compound H, (1.7 g, 7 mmol) is dissolved in anhydrous THF (50 mL) and cooled to −78° C. Add fresh LDA (1.2 eq.) as a THF solution (10 mL) and stir for 45 min. at −78° C. Add, dropwise, fluorophenoxacetaldehyde (1.3 g, 1.2 eq.) in THF (5 mL) and stir for 4 h. Warm the reaction mixture to 0° C. and quench with aqueous $NH_4Cl$ (50 mL). Extract with ether (200 mL), dry the organic phase over $MgSO_4$, filter and concentrate. Purify the resultant residue by silica gel flash chromatography, eluting with hexane→15% EtOAc/hexane. NMR and chromatographic analysis show that 7A is the same as the product of Example 1, and 7B is the same as the product of Example 3.

EXAMPLE 8

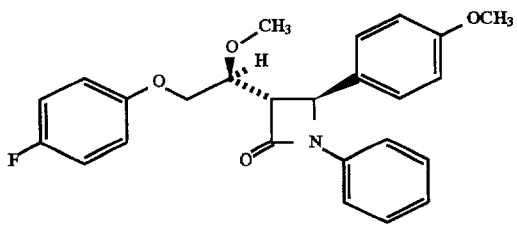

Treat a solution of the product of Example 1, Step 3 (0.15 g, 0.37 mmols) in THF with a suspension of NaH (0.017 g of 60% in oil, 0.42 mmols) at room temperature. After 15 min., add $CH_3I$ (0.07 mL, 1.12 mmols) with stirring and keep at room temperature for 16 h. Dilute the mixture with EtOAc, extract with brine, dry the organic layer over $NaSO_4$ and evaporate the solvent under vacuum. Purify the resultant oil by preparative thick layer chromatography on silica gel, eluting with EtOAc/hexane (1:3) to obtain 60 mg of the title compound. HRMS FAB (M+1): calc. 422.1768; obs. 422.1763.

EXAMPLE 9

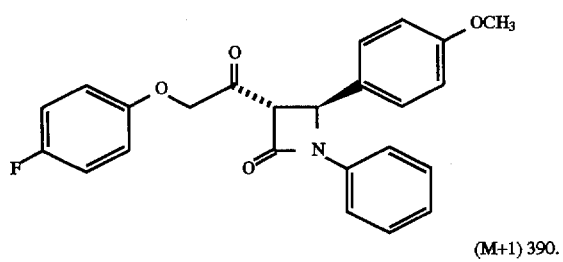

(M+1) 390.

Treat a solution of the product of Example 1, Step 3 (0.3 g, 0.7 mmols) in $CH_2Cl_2$ with pyridinium chlorochromate (0.55 g, 2.5 mmols) and basic alumina (0.4 g). Stir at room temperature for 3 days, filter through a pad of celite and wash with $CH_2Cl_2$. Purify the product by silica gel chromatography, eluting with EtOAc/hexane (1:3) to obtain 0.23 g of the title compound. HRMS FAB (M+1): calc. 406.1455; obs. 406.1422.

EXAMPLE 10

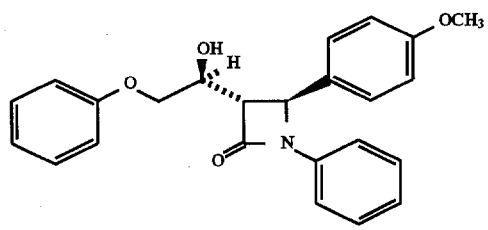

Treat the epoxide of Example 1, Step 2 (compound B-1) in a manner similar to that described in Example 1, Step 3, substituting phenol for 4-fluorophenol, to obtain the title compound, m.p. 132°–135° C., MS FAB: (M+1) 390.

EXAMPLE 11

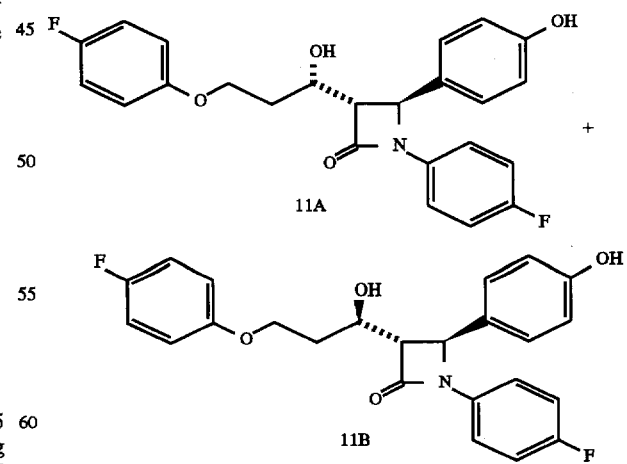

Treat the azetidinone of Preparation 1 according to the procedure described in Example 7, followed by removal of the benzyl protecting group as described in Example 2, step 3, to obtain the title compounds.

Isomer A: m.p. 147°–150° C.; HRMS FAB (M+1): calc'd. 426.1517, obs. 426.1520.

Isomer B: m.p. 146°–148° C.; HRMS FAB (M+1): calc'd. 426.1517, obs. 426.1508.

EXAMPLE 12

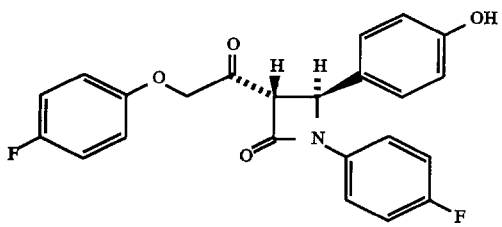

Treat the product of Example 2, step 2, according to the procedure described in Example 9, followed by removal of the benzyl protecting group as described in Example 2, step 3, to obtain the title compound: m.p. 129°–130° C.; HRMS FAB (M+1): calc'd. 410.1216, obs. 410.1204.

EXAMPLE 13

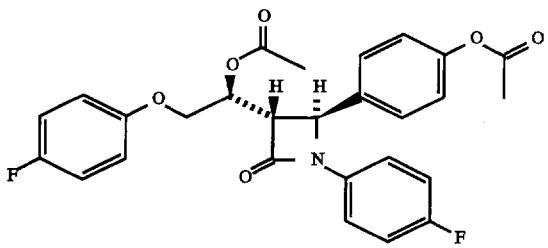

To a solution of enantiomer B from Example 2 (0.025 g, 0.06 mmole) and pyridine (0.024 mL, 0.296 mmole) in $CH_2Cl_2$ (5 mL), add excess acetyl chloride (0.01 mL, 0.14 mmole) and stir for 2 h at room temperature. Dilute the minute with $CH_2Cl_2$, wash with water and brine, dry over $Na_2SO_4$ and evaporate the solvent. Purify the resultant oil by preparative HPLC, eluting with EtOAc:hexane (1:3) to obtain the title compound: HRMS calc'd: 496.1558; found: 496.1572.

The following formulations exemplify some of the dosage forms of this invention. In each, the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

The in vivo activity of the compounds of formula I can be determined by the following procedure.

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the presence of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by 1M injection of ketamine and sacrificed by decapitation. Blood is collected into vacutainer tubes containing EDTA for plasma lipid analysis and the liver excised for tissue lipid analysis. Data is reported as percent reduction of lipid versus control.

Using the hamster in vivo test procedures substantially as described above, the following data were obtained. Compounds are referred to in the following table by the corresponding example numbers. Data is reported as percent change versus control, therefore, negative numbers indicate a positive lipid-lowering effect.

| | % Reduction | | |
|---|---|---|---|
| Ex. No. | Serum Cholesterol | Cholesterol Esters | Dose mg/kg |
| 1 | −51 | −94 | 10 |
| | −14 | −73 | 3 |
| | −14 | −57 | 1 |
| 1 (enant.A) | 0 | 0 | 10 |
| 1 (enant.B) | −44 | −96 | 10 |
| | −54 | −96 | 3 |
| | −31 | −84 | 1 |

25

-continued

| Ex. No. | % Reduction Serum Cholesterol | Cholesterol Esters | Dose mg/kg |
|---|---|---|---|
| 2 | -17 | -91 | 10 |
|  | -47 | -96 | 3 |
|  | -14 | -38 | 1 |
| 2A | 0 | 19 | 1 |
| 2B | -22 | -73 | 1 |
| 3 | 0 | -48 | 10 |
| 4 | 0 | -42 | 10 |
| 5A1 | -12 | -71 | 10 |
| 5A2 | 0 | -27 | 10 |
| 5B | 0 | -23 | 8 |
| 6b | 0 | -39 | 10 |
| 6c | -11 | 0 | 1 |
| 8 | -28 | -86 | 10 |
| 9 | — | -92 | 10 |
| 10 | — | -64 | 10 |
| 11A | 0 | -15 | 10 |
| 11B | 0 | -25 | 10 |
| 12 | -9 | -27 | 1 |
| 13 | -39 | -92 | 3 |

I claim:

1. A process for preparing a chiral β-amino ester of the formula

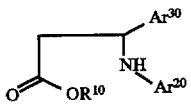

wherein:

$Ar^{20}$ is $Ar^2$, a suitably protected hydroxy-substituted aryl or a suitably-protected amino-substituted aryl;

$Ar^2$ is $R^4$-substituted aryl;

$Ar^{30}$ is $Ar^3$, a suitably protected hydroxy-substituted aryl or a suitably-protected amino-substituted aryl;

$Ar^3$ is $R^5$-substituted aryl;

$R^5$ is 1–3 substituents independently selected from the group consisting of —$OR^6$, —$O(CO)R^6$, —$O(CO)$

26

$OR^9$, —$O(CH_2)_{1-5}OR^9$, —$O(CO)NR^6R^7$, —$NR^6R^7$, —$NR^6(CO)R^7$, —$NR^6(CO)OR^9$, —$NR^6(CO)NR^7R^8$, —$NR^6SO_2$-lower alkyl, —$NR^6SO_2$-aryl, —$CONR^6R^7$, —$COR^6$, —$SO_2NR^6R^7$, $S(O)_{0-2}$-alkyl, $S(O)_{0-2}$-aryl, —$O(CH_2)_{1-10}$—$COOR^6$, —$O(CH_2)_{1-10}CONR^6R^7$, o-halogeno, m-halogeno, o-lower alkyl, m-lower alkyl, -(lower alkylene)-$COOR^6$ and —$CH$=$CH$—$COOR^6$;

$R^4$ is 1–3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and

—$C(O)OR^{10}$ is an acyl radical of a chiral alcohol of the formula $R^{10}OH$ selected from the group consisting of 1-menthyl, isopino-campheyl, (1S)-endo-bornyl, isomenthyl, trans-2-phenylcyclo-hexyl or phenylmenthyl;

comprising reacting a bromoacetate of the formula $R^{10}OC(O)CH_2Br$, wherein $R^{10}OC(O)$— is as defined above, an imine of the formula $Ar^{20}$—N=CH—$Ar^{30}$, wherein $Ar^{20}$ and $Ar^{30}$ are as defined above, and zinc in an inert solvent at a temperature of 10° to 30° C., optionally in the presence of a zinc activating agent and optionally with ultrasonification.

2. The process of claim 1 wherein the solvent is dioxane, tetrahydrofuran or diethyl ether.

3. The process of claim 1 wherein a zinc activating agent is present.

4. The process of claim 3 wherein the zinc activating agent is iodine.

5. The process of claim 4 wherein the reaction is carried out with ultrasonification.

6. The process of claim 1 wherein the reaction is carried out with ultrasonification.

* * * * *